United States Patent [19]
Plessix et al.

[11] Patent Number: 5,932,194
[45] Date of Patent: Aug. 3, 1999

[54] UV-PHOTOPROTECTIVE COSMETIC COMPOSITIONS COMPRISING POLYMER PARTICULATES/FATTY PHASES HAVING UNIQUE REFRACTIVE INDICES

[75] Inventors: Hervé Plessix, Bourg la Reine; Jean Mondet, Aulnay Sous Bois; Jean de Rigal, Claye Souilly, all of France

[73] Assignee: Societe L'Oreal S.A., Paris, France

[21] Appl. No.: 09/034,229

[22] Filed: Mar. 4, 1998

[30] Foreign Application Priority Data

Mar. 10, 1997 [FR] France ................................. 97 02800

[51] Int. Cl.$^6$ ............................... A61K 7/42; A61K 7/44
[52] U.S. Cl. ................................ 424/59; 424/60; 424/400
[58] Field of Search ........................... 424/400, 401, 424/59–60, 501; 514/938–39, 943; 252/311

[56] References Cited

U.S. PATENT DOCUMENTS 5,733,531  3/1998  Mitchnick et al. .

FOREIGN PATENT DOCUMENTS

| 0268938 | 6/1988 | European Pat. Off. . |
| 0503922 | 9/1992 | European Pat. Off. . |
| 0681830 | 11/1995 | European Pat. Off. . |
| 0755670 | 1/1997 | European Pat. Off. . |
| 95/09895 | 4/1995 | WIPO . |

*Primary Examiner*—Edward J. Webman
*Attorney, Agent, or Firm*—Burns, Doane, Swecker & Mathis, L.L.P.

[57] ABSTRACT

Topically applicable cosmetic/dermatological composition well suited for improved photoprotection of human keratinous substrates, for example human skin and/or hair, comprise (a) an aqueous phase, (b) at least one fatty phase having a refractive index $n_1$, (c) an effective UV-photoprotecting amount of at least one water-soluble UV-screening active agent, and (d) particulates of at least one non-film-forming polymer having a refractive index $n_2$, and the refractive indices $n_1$, and $n_2$ being selected such that:

$$|n_2-n_1| \leq 0.07.$$

23 Claims, No Drawings

UV-PHOTOPROTECTIVE COSMETIC COMPOSITIONS COMPRISING POLYMER PARTICULATES/FATTY PHASES HAVING UNIQUE REFRACTIVE INDICES

CROSS-REFERENCE TO PRIORITY APPLICATION

This application claims priority under 35 U.S.C. §119 of FR-02800, filed Mar. 10, 1997, hereby expressly incorporated by reference.

BACKGROUND OF THE INVENTION

1. Technical Field of the Invention

The present invention relates to novel topically applicable aqueous cosmetic compositions for the photoprotection of human keratin substrates, such as the skin, against the deleterious effects of ultraviolet radiation (these compositions hereinafter more simply designated "antisun" or "sunscreen" compositions).

This invention more specifically relates to the aforesaid sunscreen/cometic compositions comprising at least one UV-screening active agent, a dispersion of non-film-forming polymer particles having a specific refractive index and a fatty phase also having a specific refractive index, and to the use of same for those applications indicated above.

2. Description of the Prior Art

It is known to this art that light radiation of wavelengths of from 320 to 400 nm (UV-A) promotes tanning of the human epidermis; however, this radiation also causes damage to the epidermis, especially in the case of pale skin or a skin which is sensitive to UV, or in the case of skin which is continuously exposed to solar radiation. U-VA, in particular, causes a loss in the elasticity of the skin and the appearance of wrinkles, promoting premature aging thereof.

It is also known to this art that light radiation of wavelengths of from 280 to 320 nm (U-VB) causes skin burns and erythema which may, via inflamation, effect a certain level of aging of the skin. It is thus necessary, in order to conserve proper skin quality after exposure to UV radiation, to protect the skin during this exposure.

A wide variety of cosmetic compositions/compounds for the photoprotection of keratin substrates and substances, and in particular the skin, are known to this art. Exemplary thereof are, for example, hydrophilic or lipophilic aromatic compounds capable of absorbing in a wavelength range in the region 280–315 nm and/or in the region 315–400 nm. Sunscreen/antisun cosmetic compositions comprising nanoparticles of inorganic oxides which are capable of absorbing and/or reflecting UV are also known.

The efficacy of a sunscreen composition for photoprotecting the skin is generally reflected in terms of its sun protection factor (SPF), which is defined by the ratio of the amount of energy required to initiate erythema on skin protected by the agent for screening UV radiation to the amount of energy required to initiate erythema on unprotected skin.

Certain active species exhibiting UV-radiation-screening properties and incorporated into sunscreen formulations are potentially toxic vis-á-vis the skin or other human keratin substrates. It is generally sought to lower the risks of toxicity by reducing the amount of UV screening agent in the sunscreen formulations, while at the same time conserving the SPF level of protection against the damaging effects of UV radiation.

EP-A-681,830 describes such objective, via combining, with organic systems for screening out UV radiation, a mixture of polymers including an ethylene/vinyl acetate copolymer and an acrylic polymer in the form of particles, such as to increase the sun protection factor (SPF) thereof.

EP-A-669,124 also describes such objective by formulating a sunscreen composition comprising a combination of an organic system for screening out UV radiation and a latex of hollow particles of crosslinked polymer in dispersion.

SUMMARY OF THE INVENTION

It is now unexpectedly and surprisingly been determined that aqueous sunscreen formulations based an water-soluble UV screening agents and containing a combination of a dispersion of particles of a non-film-forming polymer having a specific refractive index and a fatty phase having another specific refractive index provide a sun protection factor (SPF) that is substantially improved when compared to the antisun formulations of the prior art which combine UV screening agents with polymer particles.

DETAILED DESCRIPTION OF BEST MODE AND SPECIFIC/PREFERRED EMBODIMENTS OF THE INVENTION

More particularly according to the present invention, the subject cosmetic or dermatological compositions comprise at least one fatty phase, an aqueous phase, a water-soluble system or active agents for screening out UV radiation and particles of a non-film-forming polymer. Characteristically, said fatty phase, which has a particular refractive index $n_1$, and said polymer particles, which also have a particular refractive index $n_2$, are selected such that:

$$|n_2-n_1| \leq 0.07.$$

Hereinafter, by the expression "system for screening out UV radiation" is intended an active agent for screening out UV radiation, comprising either a single compound for screening UV radiation, or a mixture of several compounds for screening UV radiation, for example admixture comprising a U-VA sunscreen agent and a U-VB sunscreen agent.

Also in the description which follows, the keratin substances or substrates are selected from among the skin, the scalp, the hair, the eyelashes, the eyebrows and the nails.

Too, the refractive indices $n_1$, and $n_2$ respectively relating to the oils constituting the fatty phase and to the particles of non-film-forming polymer are measured using a conventional refractometer in which the light source corresponds to the sodium line at room temperature.

The compositions of the present invention comprise at least one non-film-forming polymer in the form of particulates dispersed in an aqueous and/or organic medium. Exemplary thereof is, in particular, an aqueous/alcoholic, alcoholic or oily dispersing medium.

The non-film-forming polymer must be in the form of solid particles suspended in the particular medium, which of course excludes polymers that are soluble in said medium.

Any type of polymer that satisfies these criteria can be employed. Thus, radical polymers, polycondensates and optionally modified polymers of natural origin can be used. Exemplary are, for example, polyesters, polyesteramides, alkyds, polyacrylics, polyvinylics, polyurethanes, polystyrenes, natural or modified carbohydrate polymers and derivatives thereof, natural or modified natural proteins such as natural or modified natural globular proteins, whether alone or employed in admixture.

Preferably, polymers that are crosslinked, for example by means of multifunctional crosslinking agents, are used.

These polymers present the advantage of remaining in the form of non-film-forming particles and of being insoluble in the particular medium selected, irrespective of the chemical nature of the base polymer. Representative are, for example, polyacrylics crosslinked with acrylates or methacrylates of ethylene glycol, diethylene glycol or of alkylenes, or alternatively polycondensates crosslinked with polyisocyanates.

The dispersion preferably contains from 30% to 60% by weight of polymer solids.

The dispersed particulates of non-film-forming polymer advantageously have a particle size ranging from 3 to 700 nm and more preferably from 10 to 350 nm, which permits, on the one hand, avoiding the solubilization of the particles in the medium, and, on the other, improving the stability of the composition in which the particles do not settle out, while at the same time properly diffusing radiation.

In the compositions according to the invention, the polymer is preferably present in proportion of from 0.5% to 30% by weight of solids and more preferably from 2% to 15% by weight relative to the total weight of the composition.

The dispersion of particles of non-film-forming polymer can be prepared according to any of the techniques known to the prior art. Particularly exemplary is emulsion polymerization which makes it possible to obtain elementary particles of variable size with a very low polydispersity around this size.

The compositions in accordance with the invention contain water-soluble systems for screening out UV radiation, and representative thereof, for example, are para-aminobenzoic acid and salts thereof, anthranilic acid and salts thereof, salicylic acid and salts thereof, cinnamic acid derivatives and salts thereof, sulfonic derivatives of benz-x-azole (benzothiazoles, benzimidazoles, benzoxazoles) and salts thereof, sulfonic derivatives of benzophenone and salts thereof, sulfonic derivatives of benzylidenecamphor and salts thereof, benzylidenecamphor derivatives substituted by a quaternary amine and salts thereof, phthalydenecamphor-sulfonic acid derivatives and salts thereof, sulfonic derivatives of benzotriazole, nanoparticles of inorganic oxides surface-treated such as to be hydrophilic, and mixtures thereof.

Hydrophilic polymers having, in addition and taking account of their chemical nature, properties of photoprotection against UV radiation can also be used. Exemplary are polymers containing substituted or unsubstituted benzylidenecamphor and/or benzotriazole groups. It should, however, be noted that the SPF of these polymers is not sufficient to permit them to be considered as UV screening agents.

The hydrophilic UV screening agent(s) are present in the compositions of the invention at concentrations preferably ranging from 0.1% to 30% by weight, more preferably from 0.5% to 25% by weight, relative to the total weight of the composition.

The fatty phase of the compositions of this invention can contain one or more oils, preferably selected from the group consisting of:

(a) mineral oils such as liquid paraffin and liquid petroleum jelly;

(b) hydrocarbon oils containing aromatic rings, such as benzoic acid esters, for example the commercial products Finsolv marketed by Finetex, for instance those defined below:

FINSOLV TN: $C_{12}$–$C_{15}$, alkyl benzoate
FINSOLV SB: isostearyl benzoate
FINSOLV BOD: octyidodecyl benzoate;

(c) polyglycerol esters such as polyglyceryl-2 diisostearate and polyglyceryl-2 triisostearate;

(d) oils of animal origin such as perhydrosqualene and squalane;

(e) oils of plant origin such as sweet almond oil, avocado oil, castor oil, olive oil, jojoba oil, sesame oil, groundnut oil, macadamia oil, grapeseed oil, rapeseed oil, coconut oil, muscat rose oil, triolein oil and more particularly triglycerides having a large content of unsaturated fatty acids;

(f) synthetic oils such as purellin oil and isoparaffins;

(g) fluoro and perfluoro oils such as perfluorodecalin, perfluoro polyethers, such as the products Fomblin HC 04, Fomblin HC 25 and Fomblin HC R marketed by Montedison;

(h) fatty acid esters such as purcellin oil, octyldodecyl neodecanoate, isodecyl isononanoate, isononyl isononanoate, octyldodecyl neopentanoate, isopropyl myristate and isopropyl palmitate;

(i) high-molecular-weight polyolefins such as polybutenes or polydecenes;

(j) fatty alcohols such as octyldodecanol and oleyl alcohol;

(k) linear, branched or cyclic, volatile or non-volatile silicones which either may or may not be organomodified, such as the product Silbione 70 641 V200 (diphenyldimethicone) marketed by Rhône-Poulenc or the products DC 556 (phenyltrimethicone) and SF 558 (methylphenylpolysiloxane) marketed by Dow Corning; volatile cyclic silicones or non-volatile linear polydimethylsiloxanes.

In known manner, all of the compositions of the invention can contain additives and adjuvants that are common in the cosmetic and dermatological fields, including other standard gelling agents or thickeners; polymers; moisturizers; emollients; hydrophilic or lipophilic active agents such as ceramides; anti-free-radical agents; weight-reducing active agents; bactericides; sequestering agents; antidandruff agents; antioxidants; preservatives; basifying or acidifying agents; fragrances; fillers; mineral, synthetic, plant or animal waxes, pasty fatty substances; organic solvents; softeners; complementary sunscreens; anti-foaming agents; surfactants; self-tanning agents; propellants; dyes, pigments and colorants, etc. The amounts of these various additives and adjuvants are those conventional to the particular fields or fields.

It will of course be appreciated that one skilled in this art will take care to select the optional compound(s) to be added to the compositions, of the invention such that the advantageous properties intrinsically associated therewith are not, or are not substantially, adversely affected by the addition envisaged.

The compositions according to the invention are advantageously formulated as serums, milks, more or less smooth creams or pastes, and the like. These compositions are prepared according to conventional techniques.

The compositions of the present invention are advantageously in liquid, pasty or solid form, for example in the form of a gel, an oil-in-water or water-in-oil emulsion, an ointment, or a mousse.

The compositions according to this invention can also be formulated as care products, such as creams; as makeup products such as foundations, face powders, lipsticks, mascaras or eyeliners; as hair products such as rinse-out or leave-in gels, lotions or shampoos.

The compositions of the invention can also be used as products for protecting keratin substances against UV radiation, and in particular the skin.

Thus, the invention also features a cosmetic treatment for protecting human keratin substrates, in particular the skin and/or hair, against UV radiation, this regime or regimen comprising topically applying an effective amount of a composition as described above to the keratin support.

In order to further illustrate the present invention and the advantages thereof, the following specific examples are given, it being understood that same are intended only as illustrative and in nowise limitative.

EXAMPLE 1

Preparation of a dispersion of non-film-forming particles of acrylic polymer

Composition of the polymer

| (a) methyl methacrylate | 91% by weight |
| --- | --- |
| (b) methacrylic acid | 5% by weight |
| (c) ethylene glycol dimethacrylate (crosslinking agent) | 4% by weight |

Procedure 100 g of deionized water, 16 g of active material, i.e., an alkyl ethoxy sulfate surfactant marketed under the trademark Abex JKB by Rhône-Poulenc and 2.5 g of potassium persulfate were introduced into a reactor fitted with a central mechanical stirrer, a thermometer and a condenser. The mixture was heated to a temperature of 80° C. with rapid stirring.

In parallel, the two "pouring" solutions $S_1$, and $S_2$ described below were prepared:

Pouring solution $S_1$, (monomer solution)

| (a) methyl methacrylate | 1,820 g |
| --- | --- |
| (b) methacrylic acid | 100 g |
| (c) ethylene glycol dimethacrylate (crosslinking agent) | 80 g |

Pouring solution $S_2$

| (a) deionized water | 5,000 g |
| --- | --- |
| (b) Abex JKB | 160 g |
| (c) potassium persulfate | 7.5 g |

When the aqueous solution in the reactor had reached a temperature of 80° C., 10% of the solution $S_1$ was added and the mixture was permitted to react for 15 minutes. The remainder of the solution $S_1$ and the solution $S_2$ were then poured in simultaneously over a period of 4 hours, at a constant flow rate. At the end of the two simultaneous additions, the temperature of the reaction medium was increased to 85° C. and was maintained at this temperature for 30 minutes.

The mixture was permitted to cool to room temperature with stirring. It was filtered through a nylon gauze.

A dispersion of polymer particles having the following characteristics was obtained:

(1) Average particle size: 110 nm.
(2) Particle size polydispersity measured by quasi-elastic light scattering using a Coulter N4 SD type machine: <0.1.
(3) Dry extract in a ventilated oven at 80° C. to constant weight: 27%.
(4) Refractive index $n_2$=1.49.
(3) Dry extract in a ventilated oven at 80° C. to constant weight: 27%.
(4) Refractive index $n_2$=1.59.

EXAMPLES 3–7

(Comparative sunscreen formulations)

The five oil-in-water emulsions 1 to 5 below were formulated:

SUNSCREEN EMULSION 1

(Example 3, according to invention)

| (a) Polyacrylic latex according to Example 1 ($n_2$ = 1.49) | 10% by weight (*A.M.) |
| --- | --- |
| (b) Castor oil ($n_1$ = 1.48) | 20% by weight |
| (c) 4-(4,7,7-Trimethyl-3-oxabicyclo-[2.2.1]hept-2-ylidenemethyl)-benzenesulfonic acid marketed under the trademark Mexoryl SL by Chimex as an aqueous 50% solution, the pH of which was adjusted to 7 with triethanolamine (water-soluble UV screening agent) | 10% by weight |
| (d) Polyoxyethylenated and polyoxy-propylenated surfactant marketed under the trademark Symperonic PE/PBS by ICI Americas | 5% by weight |
| (e) Water | 55% by weight |

*A.M. = active material

EXAMPLE 2

Preparation of a dispersion of non-film-forming particles of crosslinked polystyrene The reactants indicated below were introduced into a 1-liter cylindrical reactor fitted with a central stirrer, a condenser, a thermometer and a nitrogen sparge:

| (a) styrene | 98 g |
| --- | --- |
| (b) divinylbenzene (crosslinking agent) | 2 g |
| (c) nonylphenol polyoxyethylenated with 25 EO marketed under the trademark AD 33 by Seppic | 0.0735 g A.M. |
| (d) potassium persulfate | 0.175 g |
| (e) deionized water | 70 g |

The aqueous solution was first prepared with the water, the surfactant and the crosslinking agent with stirring and sparging with nitrogen, after which the monomer was added. The stirring was adjusted to 300 revolution/min. The reaction medium was heated to 72° C. and was maintained at this temperature for 6 hours. The temperature was then increased to 85° C. over 1 hour. It was returned to room temperature and filtered through a sieve.

A dispersion of polymer particles having the following characteristics was obtained:

(1) Average particle size: 60 nm.
(2) Particle size polydispersity measured by quasi-elastic light scattering using a Coulter N4 SD type machine: <0.1.

SUNSCREEN EMULSION 2

(Example 4, not according to invention)

| | |
|---|---|
| (a) Polystyrene latex according to Example 2 ($n_2$ = 1.59) | 10% by weight (A.M.) |
| (b) Castor oil ($n_1$ = 1.48) | 20% by weight |
| (c) 4-(4,7,7-Trimethyl-3-oxobicyclo-[2.2.1]hept-2-ylidenealethyl)-benzenesulfonic acid marketed under the trademark Mexoryl SL by Chimex, as an aqueous 50% solution, the pH of which was adjusted to 7 with triethanolamine (water-soluble UV screening agent) | 10% by weight |
| (d) Polyoxyethylenated and polyoxy-propylenated surfactant marketed under the trademark Symperonic PE/P85 by ICI Americas | 5% by weight |
| (e) Water | 55% by weight |

SUNSCREEN EMULSION 3

(Example 5, not according to the invention)

| | |
|---|---|
| (a) Polystyrene latex according to Example 2 ($n_2$ = 1.59) | 10% by weight (A.M.) |
| (b) Diisopropyl adipate ($n_1$ = 1.423) | 20% by weight |
| (c) 4-(4,7,7-Trimethyl-3-oxobicyclo-[2.2.1]hept-2-ylidenemethyl)-benzenesulfonic acid marketed under the trademark Mexoryl SL by Chimex, as an aqueous 50% solution, the pH of which was adjusted to 7 with triethanolamine (water-soluble UV screening agent) | 10% by weight |
| (d) Polyoxyethylenated and polyoxy-Propylenated surfactant marketed under the trademark Symperonic PE/P85 by ICI Americas | 5% by weight |
| (e) Water | 55% by weight |

LATEX-FREE SUNSCREEN EMULSION 4

(Example 6, not according to invention)

| | |
|---|---|
| (a) Castor oil ($n_1$ = 1.48) | 20% by weight |
| (b) 4-(4,7,7-Trimethyl-3-oxobicyclo-[2.2.1]hept-2-ylidenemethyl)-benzenesulfonic acid marketed under the trademark Mexoryl SL by Chimex, as an aqueous 50% solution, the pH of which was adjusted to 7 with triethanolamine (water-soluble UV screening agent) | 10% by weight |
| (c) Polyoxyethylenated and polyoxy-propylenated surfactant marketed under the trademark Symperonic PE/P85 by ICI Americas | 5% by weight |
| (d) Water | 65% by weight |

UV-SCREENING-AGENT-FREE EMULSION 5

(Example 7, not according to invention)

| | |
|---|---|
| (a) Polyacrylic latex according to Example 1 ($n_2$ = 1.49) | 10% by weight (A.M.) |
| (b) Diisopropyl adipate ($n_1$ = 1.423) | 20% by weight |
| (c) Polyoxyethylenated and polyoxy-propylenated surfactant marketed under the trademark Symperonic PE/P85 by ICI Americas | 5% by weight |
| (d) Water | 65% by weight |

Mode of formulation of the emulsions 1 to 3 and 5

The surfactant was dispersed in the water at room temperature in the presence of the water-soluble UV screening agent in a 30 ml screw-top flask. The oil was heated to 70° C. and then poured into the aqueous phase. The constituents present in the mixture obtained were stirred at 70° C. using a mechanical stirring device for 5 minutes at 18,000 revolutions/minute. The emulsion was then permitted to cool to room temperature. This emulsion was then treated with ultrasound. Pulses and non-pulses were alternated every second for 10 minutes. At the end of the preparation of the emulsion, the latex was added, at room temperature, and the entire mixture was then homogenized using a Vortex-type homogenization machine.

EXAMPLE 8: Tests of Sun Protection Factor

GENERAL PRINCIPLE

The protection factor on the skin against UV radiation was determined relative to each of the emulsions 1 to 5 as described above according to the technique and with the apparatus described in the published French patent application FR-A-2,719,989.

According to this method, the spectrum was recorded in vivo by reflection. Irrespective of the light incident on the skin, one portion was reflected specularly by the surface in all directions of space and contained no spectral information; another fraction penetrated into the skin, was scattered on the internal structures and emerged therefrom isotropically. This energy contained spectral information regarding the layers through which it had passed, and in particular regarding the screening formulation applied to the surface. It was this energy which had to be selected and measured. Polarized light was employed.

The incident light E($\lambda$) was polarized in the plane of incidence, the scattered light ED($\lambda$) was measured perpendicularly to the surface of the skin at the outlet of a polarizer perpendicular to the plane of incidence and the reflected light ER($\lambda$) was measured at the outlet of a polarizer which was parallel relative to the plane of incidence. An absorbance spectrum for the skin, referred to as the "pseudo-brilliance spectrum" was thus determined by the ratio ER($\lambda$)/ED($\lambda$).

The apparatus included a xenon lamp and a monochromator downstream thereof which was coupled to an optical fiber which entered the measuring probe. Two optical fibers exited this probe and contained respectively, the scattered light and the light reflected towards the photomultipliers and their associated electronics. The apparatus was controlled by a computer.

The protection factor of each antisun or sunscreen composition was calculated according to the following formula:

$$I = \Sigma_i \alpha_i DB_i K_i$$

in which $\alpha_1$, denotes the erythemal efficacy coefficient according to the COLIPA standard in the given wavelength range i; $DB_i$ is the variation in pseudo-brilliance in the given wavelength range i and $K_i$ is the correction factor which made it possible to convert the spectrum of the lamp used into a solar spectrum in the given wavelength range i.

The coefficients $\alpha_1$ and $K_i$ are well known to this art relating to sunscreens and are described, in particular, in the article "A comparison of in vivo and in vitro testing of sunscreen formula" in *Photochem. and Photobiol.*, Vol. 29, pp. 559–566 (1978) and in "SPF test methods", January 1984 from COLIPA.

The protection factor I thus obtained can be compared with the protection index (SPF: Sun Protection Factor) which is typically given to commercial sunscreen products.

EXPERIMENTAL PROTOCOL

These measurements were carried out on the internal forearm of a group of individuals. Two measuring areas were defined on each arm and clearly delimited using the electrodes required to maintain and reposition the probe.

Each of the emulsions 1 to 5 as described above was applied to each area at a rate of 2 mg/cm$^2$ using a Gilson micropipette (48 μl per 48 cm$^2$). Before each application, the test product was rehomogenized by mechanical stirring.

The wavelength range i employed was 280–400 nm. The brilliance spectrum measurements were carried out in the said range in 5 nm steps. These were carried out before application and 15 minutes after application in order to reduce the fluctuations in the results obtained. The measuring sessions were spaced at least 48 hours apart in order for the skin not to have any residual trace of product.

All of the antisun products were tested on the same group of individuals in order for the results obtained not to be affected by any individual effects.

The average sun protection factor I was calculated for each emulsion 1 to 5 on the group of individuals tested. The results obtained are reported in the Table below:

TABLE

| Emulsion tested | Refractive index $n_1$ of the latex employed | Refractive index $n_2$ of the fatty phase | $\|n_2-n_1\|$ | Average sun protection factor $\Sigma_i\, \alpha_i\, DB_i\, K_i$ |
|---|---|---|---|---|
| 1 (invention) | 1.49 | 1.48 | 0.01 | 78 |
| 2 (not in accordance with the invention) | 1.59 | 1.48 | 0.11 | 22 |
| 3 (not in accordance with the invention) | 1.59 | 1.42 | 0.17 | 27 |
| 4 latex-free (not in accordance with the invention) | — | 1.48 | — | 23 |
| 5 UV-screening-agent-free (not in accordance with the invention) | 1.49 | 1.42 | 0.01 | 2.6 |

These results plainly evidence that the sunscreen emulsion 1 according to the invention containing a latex having a refractive index $n_1$, and a fatty phase having a refractive index $n_2$ selected such that $|n_2-n_1|\leq 0.07$ (i.e.: 0.01) had an average sun protection factor which was considerably higher than that of the sunscreen emulsions 2 and 3 containing a latex and a fatty phase such that $|n_2-n1|$ was, respectively, equal to 0.11 and 0.17.

These results also indicate that the sunscreen emulsions 2 and 3 containing a latex and a fatty phase such that $|n_2-n_1|$, respectively, was equal to 0.11 and 0.17, had average sun protection factors which were equivalent to that of the sunscreen emulsion 4 which contained no latex. Stated otherwise, the latex/fatty phase combinations used in emulsions 2 and 3 did not make it possible to increase the sun protection factor of an emulsion based on a water-soluble UV screening agent.

Lastly, these results evidence that the latex/fatty phase combination in accordance with the invention, used in an emulsion containing no water-soluble UV screening agents, presented virtually no UV-radiation-absorbing effect.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological composition suited for the photoprotection of human keratin, comprising (a) an aqueous phase, (b) at least one fatty phase having a refractive index $n_1$, (c) an effective UV-photoprotecting amount of at least one water-soluble UV-screening active agent, and (d) particulates of at least one non-film- forming polymer having a refractive index $n_2$, said refractive indices $n_1$ and $n_2$ being selected such that:

$$|n_2-n_1|\leq 0.07.$$

2. The cosmetic/dermatological composition as defined by claim 1, formulated into topically applicable, cosmetically/dermatologically acceptable vehicle, diluent or carrier therefor.

3. The cosmetic/dermatological composition as defined by claim 1, said at least one non-film-forming polymer comprising a radical polymer, polycondensate, or optically modified natural polymer.

4. The cosmetic/dermatological composition as defined by claim 3, said at least one non-film-forming polymer comprising a polyester, polyesteramide, alkyd, polyacrylic, polyvinylic, polyurethane, polystyrene, natural or modified carbohydrate polymer or derivative thereof, natural or modified protein, or mixture thereof.

5. The cosmetic/dermatological composition as defined by claim 1, comprising (d) particulates of at least one crosslinked non-film-forming polymer.

6. The cosmetic/dermatological composition as defined by claim 1, said at least one non-film-forming polymer comprising aqueous, aqueous/alcoholic or alcoholic dispersion thereof.

7. The cosmetic/dermatological composition as defined by claim 1, said at least one non-film-forming polymer comprising fatty phase dispersion thereof.

8. The cosmetic/dermatological composition as defined by claim 1, said particulates of said at least one non-film-forming polymer having a particle size ranging from 3 to 700 nm.

9. The cosmetic/dermatological composition as defined by claim 8, said particle size ranging from 10 to 350 nm.

10. The cosmetic/dermatological composition as defined by claim 1, said at least one non-film-forming polymer comprising from 0.5% to 30% by weight thereof.

11. The cosmetic/dermatological composition as defined by claim 10, said at least one non-film-forming polymer comprising from 2% to 15% by weight thereof.

12. The cosmetic/dermatological composition as defined by claim 1, comprising at least one hydrophilic UV-screening active species selected from among para-aminobenzoic acid or salt thereof, anthranilic acid or salt thereof, salicylic acid or salt thereof, cinnamic acid derivative or salt thereof, sulfonic derivative of benz-x-azole or salt thereof, sulfonic derivative of benzophenone or salt thereof, sulfonic derivative of benzylidenecamphor or salt thereof, benzylidene-camphor derivative substituted by a quaternary amine or salt thereof, phthalydene-camphorsulfonic acid derivative or salt thereof, sulfonic derivative of benzotriazole, or nanoparticles of an inorganic oxide.

13. The cosmetic/dermatological composition as defined by claim 1, said at least one UV-screening active agent (c) comprising from 0.1% to 30% by weight thereof.

14. The cosmetic/dermatological composition as defined by claim 13, said at least one UV-screening active agent (c) comprising from 0.5% to 25% by weight thereof.

15. The cosmetic/dermatological composition as defined by claim 1, said at least one fatty phase (b) comprising a mineral oil, aromatic hydrocarbon oil, polyglycerol ester, animal oil, plant oil, synthetic oil, fluoro or perfluoro oil, fatty acid ester, fatty alcohol, silicone, or organomodified silicone.

16. The cosmetic/dermatological composition as defined by claim 1, comprising (c) at least one UV-A screening active agent and at least one UV-B screening active agent.

17. The cosmetic/dermatological composition as defined by claim 2, comprising an emulsion.

18. The cosmetic/dermatological composition as defined by claim 2, comprising a serum, milk, cream, paste, gel, ointment, lotion or mousse.

19. The cosmetic/dermatological composition as defined by claim 2, comprising a skincare, haircare, or makeup formulation.

20. The cosmetic/dermatological composition as defined by claim 19, comprising a skin cream, foundation, face powder, lipstick, mascara, eyeliner, hair gel, hair lotion, or shampoo.

21. The cosmetic/dermatological composition as defined by claim 1, further comprising a fat, organic solvent, thickening or gelling agent, softener, antioxidant, opacifying agent, stabilizing agent, emollient, silicone, α-hydroxy acid, anti-foaming agent, hydrating agent, vitamin, hydrophilic or lipophilic active agent, bactericide, weight-reducing active agent, antidandruff agent, anti-free-radical agent, wax, paste, complementary sunscreen, self-tanning agent, fragrance, preservative, surfactant, filler, sequestering agent, polymer, propellant, insect repellent, basifying or acidifying agent, dye, colorant, pigment, or mixture thereof.

22. A method for protecting a human keratinous substrate against the deleterious effects of ultraviolet radiation, comprising topically applying thereto an effective photoprotecting amount of the cosmetic/dermatological composition as defined by claim 1.

23. The method as defined by claim 1, comprising photoprotecting human skin, scalp, hair, eyelashes, eyebrows, and/or nails.

* * * * *